United States Patent [19]
Lewis

[11] Patent Number: 4,789,336
[45] Date of Patent: Dec. 6, 1988

[54] ART OF PROTECTING A DENTAL INSTRUMENT

[76] Inventor: Cheri Lewis, 240 S. La Cienega Blvd., Beverly Hills, Calif. 90211

[21] Appl. No.: 66,694

[22] Filed: Jun. 25, 1987

[51] Int. Cl.$^4$ .............................................. A61C 1/16
[52] U.S. Cl. .................................................. 433/116
[58] Field of Search ....................................... 433/116

[56] References Cited

U.S. PATENT DOCUMENTS

| | | | |
|---|---|---|---|
| 1,162,941 | 12/1915 | Martin et al. | 433/116 |
| 1,342,968 | 6/1920 | Moolten | 433/116 |
| 4,253,831 | 3/1981 | Eaton | 433/116 |
| 4,693,871 | 9/1987 | Geller | 433/116 |

FOREIGN PATENT DOCUMENTS 463542  7/1928  Fed. Rep. of Germany ...... 433/116

*Primary Examiner*—Robert Peshock
*Attorney, Agent, or Firm*—Dominick Nardelli

[57] ABSTRACT

A sterilized protective sleeve in combination with a rigid shield for the handle of a dental instrument is disclosed wherein the sleeve consists of an elastic tubular casing adapted to conform to the shank of the instrument. The rigid shield is contoured to conform to the head end of the instrument and has an opening through which the rotating burr of the instrument protrudes. Furthermore, one of the open ends of the casing is capable of receiving or extending over both the rigid shield and the shank of the dental instrument so that the rotating burr extends out of the other open end of the casing. In particular, the opening in the rigid shield is made slightly larger than the shank of the burr so that minimal clearance is provided to minimize contamination.

6 Claims, 1 Drawing Sheet

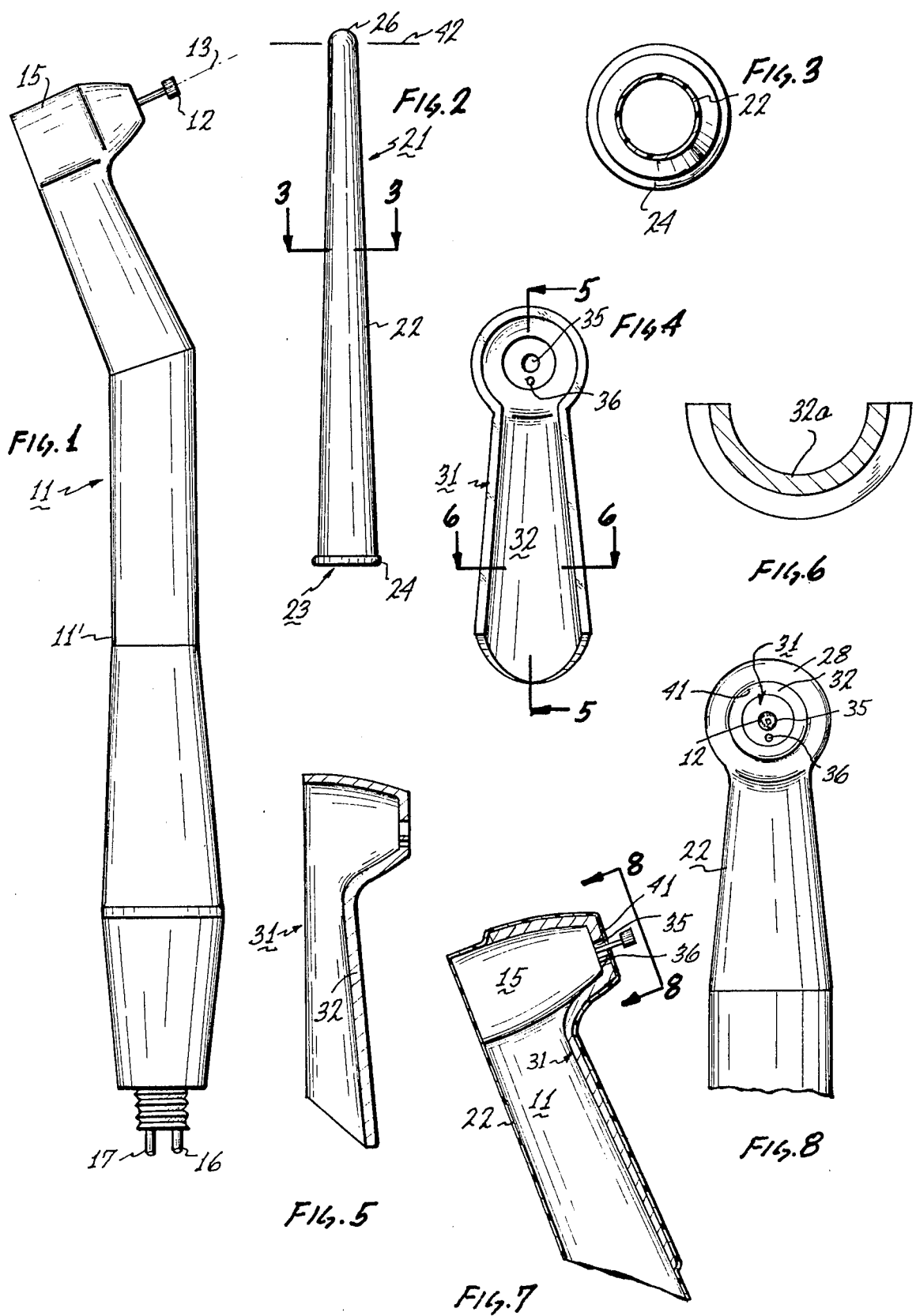

ART OF PROTECTING A DENTAL INSTRUMENT

BACKGROUND OF THE INVENTION

1. Field of the Invention

This invention relates to the art of providing means for ensuring that a dental instrument is in a better sterilized condition before use.

2. Description of the Prior Art

Scrupulous hygiene is of utmost importance in the mouth to avoid infection of the mouth cavity of the patient. With the advent of an ultra-high speed, turbine-driven, drill heat treatment of the instruments for sterilization is out of the question for several reasons. Ultra-high speed devices rely on air bearings which should be very highly polished so that a viscious air-film bearing is developed between the two moving surfaces. Heat naturally deteriorates these polished surfaces and without polished surfaces no air-film bearings could be formed. Therefore, the sterilization process becomes expensive and time consuming. The dentists then, in order to become produtive, would have to keep on hand a hundred or so of these expensive air turbine drills. For these reasons, these air drills are not fully sterilized after each use.

SUMMARY OF THE INVENTION

1. Statement

The present invention teaches the use of a protective sleeve with an elongated dental instrument having a jaw at its end which jaw is capable of gripping a rotatable burr or bit. The protective sleeve consists of an elastic and pliable tubular casing made of a thin stretchable polymer that can sufficiently stretch so it becomes taut around the dental instrument without forming any folds or creases around the sleeve area. At the jaw end of the dental instrument a rigid, disposable shield or member is disposed preferably made of plastic. The disposable member has one aperture that aligns with the shaft of the burr and if required, it has another aperture that aligns with any exit port for the cooling water which exit port may be located at the jaw end of the dental instruments. In addition, if the instrument is of the kind that has fiber optics and light ports directing illuminating light to the burr, the disposable member is made of clear transparent plastic, at least in the region of the light ports.

2. Objects

A primary object of this invention is to provide on a dental instrument an expendable sterilized exposed surface.

Another object of this invention is to provide a disposable membrane that is capable of being stretched around a dental instrument with the addition of means for providing an effective steril seal around the rotating bit.

BRIEF DESCRIPTION OF THE DRAWING

FIG. 1 is a side view of one of the standard dental instruments which could be used with my novel protective means.

FIG. 2 is a side elevation of my novel protective sleeve which is symetrical about an axis and is to be used with the instrument shown in FIG. 1.

FIG. 3 is a cross-section view of the sleeve shown taken on line 3—3 of FIG. 2 and in the direction of the arrows.

FIG. 4 is a plan view of my novel protective shield to be used with the instrument shown in FIG. 1.

FIG. 5 is an axial cross-section taken on line 5—5 of FIG. 4 and in the direction of the arrows.

FIG. 6 is a cross-section taken on line 6—6 of FIG. 4 and in the direction of the arrows.

FIG. 7 is a partial and side view of the head portion of the instrument, shown in FIG. 1 with the shield of FIG. 4 next to the head portion and the sleeve of FIG. 2 covering the instrument and the shield, the shield and sleeve being shown in cross-section.

FIG. 8 is a view taken on line 8—8 of FIG. 7 and in the direction of the arrows.

DESCRIPTION OF THE PREFERRED EMBODIMENT

Referring to FIG. 1, in particular, there is shown a typical standard dental instrument 11 which is well known in the art, as indicated in U.S. Pat. No. 4,166,935. The instrument has a shank 11 shaped to conform to the contour of one's hand. On one end of the shank 11' is suitably mounted a tooth treating tool 12 which in this case is a burr or bit and rotatable about its axis depicted by line 13. The end of the shank 11 which carries the tool 12 is called a head 15 within which is disposed the high speed turbine which rotates the tool 12 in a manner well known in the art. At the lower or other end of the shank 11 is formed a coupling means so that air can be forced through a tube 16 to drive the turbine and so that water can be forced through a tube 17 to be jetted out of a suitable port (not shown) in the head 15. The port can be formed so that the water can be jetted to the tool 12 to cool it during operation. One understands that some dental instruments do not have a port through which water is jetted.

Referring to FIGS. 2 and 3, there is shown a protective sleeve 21 made of an elastic, pliable and stretchable, rubber-like material commonly referred to as latex. The sleeve 21 has a tubular body 22, which has an open end 23 around which is formed an annular bead 24 for convenience as will become apparent hereinafter. The body 22, for convenience of manufacture, has a closed end 26 that is dome-shaped. The body 22 is circular in cross-section as shown in FIG. 4 and is made as thin as practical. The diameter of body 22 is made smaller than the diameter of the dental instrument so that, when the protective sleeve 21 is pulled over and stretched around the dental instrument to make the sleeve 21 taut, no creases are formed in it to hamper one from handling the dental instrument.

Now referring to FIGS. 4, 5 and 6, there is shown a nonstretchable, somewhat rigid shield 31 which has a shape that mates with the shape of the head 15 of the dental instrument 11. As readily visible in the drawing, a concave surface 32 on the instrument is congruent to the external surface of the head 15. For convenience the surface 32 represented by a surface 32a has a curvature of 180 degrees or less. This curvature limitation and shape allows the shield 31 to be positioned flush against the head 15 as shown in FIG. 7. The exact shape of the shield 31 can readily be determined by one skilled in the art in making a mold cavity using the instrument 11 as a master. One understands that each differently-shaped standard instrument requires a shield like the shield 31 that conforms to its shape. Making such various shields is within the skill of one skilled in the art. The shield 31 shown has an aperture 35 that is in axial alignment with the shaft of burr 12. Since the shield 31 is stiff and rigid, the clearance between the aperture 35 and the shaft of the burr 12 needs only to be sufficient to prevent friction. The shield 31 shown herein is also adopted with a port 36 which can be accurately positioned so that it is aligned with the water port (mentioned above in the head 15.) If the instrument 11 is of the type that uses a fiberoptic light source the shield 31 can be made of a light transparent plastic. Again, if the instrument 11 does not require water cooling, port 36, of course, will be eliminated.

As shown in FIG. 7 herein the sleeve 21 is shown partially broken away to show how the body 22 is taut around the dental instrument, but more particularly, its shank 11 and head 15. The cross-section illustration of FIG. 7 shows that an aperture or hole 41 is formed at the closed end 26 to allow the burr 12 to extend therethrough. Since the size of the hole 41 is difficult to predict after the sleeve 21 is stretched over the dental instrument, the shield 31 is first placed over and against the head 15 as shown in FIG. 7. The sleeve 21 being extremely stretchable one can readily position the aperture 41 also as shown in FIG. 7. The bead 23 obviously allows one to roll up the sleeve onto the head after it is manufactured so that a technician can readily cover the instrument by simply unrolling the sleeve thereover.

I claim:

1. In combination:
   a dental instrument having a handle, a head attached to the end of the handle, and means for attaching a tooth treating tool to said head,
   a shield made of a warped rigid-like sheet material having a shape that is congruent to said dental instrument so that said shield can be placed next to and flush against said head and;
   a sleeve made of an elastic, pliable and stretchable, rubber-like material with open ends capable of covering said dental instrument and shield.

2. The combination of claim 1 wherein:
   said tooth treating tool has a shaft with a burr fixed to its end;
   said tool is attached to said head by said shaft;
   said shield has an aperture so positioned to align with said shaft when said shield is placed next to said instrument.

3. The combination of claim 2 wherein:
   said instrument further includes a means for jetting water at said tool by a water port, and;
   said shield further includes a port which aligns with said water port of said means.

4. The combination of claim 3 wherein said handle has a substantially elongated shape;
   said shaft of said burr is positioned in a substantially perpendicular position to said instrument;
   said shield having a concave surface with a first portion being substantially cup-shaped and a second portion being attached to said cup-shape and being substantially semicylindrically shaped;
   said aperture and said port are formed in the bottom of said first portion.

* * * * *